United States Patent [19]
Dempsey et al.

[11] Patent Number: 5,419,337
[45] Date of Patent: May 30, 1995

[54] NON-INVASIVE MULTI-ELECTROCARDIOGRAPHIC APPARAATUS AND METHOD OF ASSESSING ACUTE ISCHAEMIC DAMAGE

[76] Inventors: George J. Dempsey, 13 Ashley Gardens, Belfast BT15 4DN; John M. Anderson, 16 Torgrange, Hollywood, Belfast BT18 0NG; Agnes A. Adgey, 20 Myrtle Field Park, Belfast, all of Northern Ireland

[21] Appl. No.: 16,528

[22] Filed: Feb. 11, 1993

[30] Foreign Application Priority Data

Feb. 14, 1992 [IE] Ireland ................ 920491

[51] Int. Cl.6 .......................................... A61B 5/0452
[52] U.S. Cl. .......................................... 128/702
[58] Field of Search ............... 128/696, 699, 702, 703, 128/710

[56] References Cited

U.S. PATENT DOCUMENTS

| | | | |
|---|---|---|---|
| 4,249,538 | 2/1981 | Musha et al. | 128/709 |
| 4,546,776 | 10/1985 | Bellin et al. | 128/704 |
| 4,680,708 | 7/1987 | Ambos et al. | 128/702 |
| 4,794,532 | 12/1988 | Leckband et al. | 128/710 |
| 4,924,825 | 5/1990 | Chamoun | 128/702 |
| 4,974,598 | 12/1990 | John | 128/702 |
| 5,046,504 | 9/1991 | Albert et al. | 128/710 |
| 5,054,496 | 10/1991 | Wen et al. | 128/696 |
| 5,085,224 | 2/1992 | Galen et al. | 128/696 |
| 5,135,004 | 8/1992 | Adams et al. | 128/696 |
| 5,146,926 | 9/1992 | Cohen | 128/710 |
| 5,215,009 | 6/1993 | Haberl et al. | 128/702 |

FOREIGN PATENT DOCUMENTS 0335977 of 1989 European Pat. Off. .

OTHER PUBLICATIONS

Borland C++ DOS Reference, Version 4.0, p. 54 copy in file.
"Combined Manual for VidC and DigC", Chirp Technical Services, Del Mar Calif., pp. 1-1 to 1-3, copy in file.

Primary Examiner—William E. Kamm
Attorney, Agent, or Firm—Sughrue, Mion, Zinn, Macpeak & Seas

[57] ABSTRACT

An apparatus for the detection, recording and analysis of the electrical activity of a cardiac comprises an array of from 40 to 100 electrodes each capable of detecting an electrical signal associated with the ST component of a heartbeat. The array is connected to a microprocessor controlled interface which in turn is connected to a microprocessor controlled analyser and display apparatus.

5 Claims, 4 Drawing Sheets

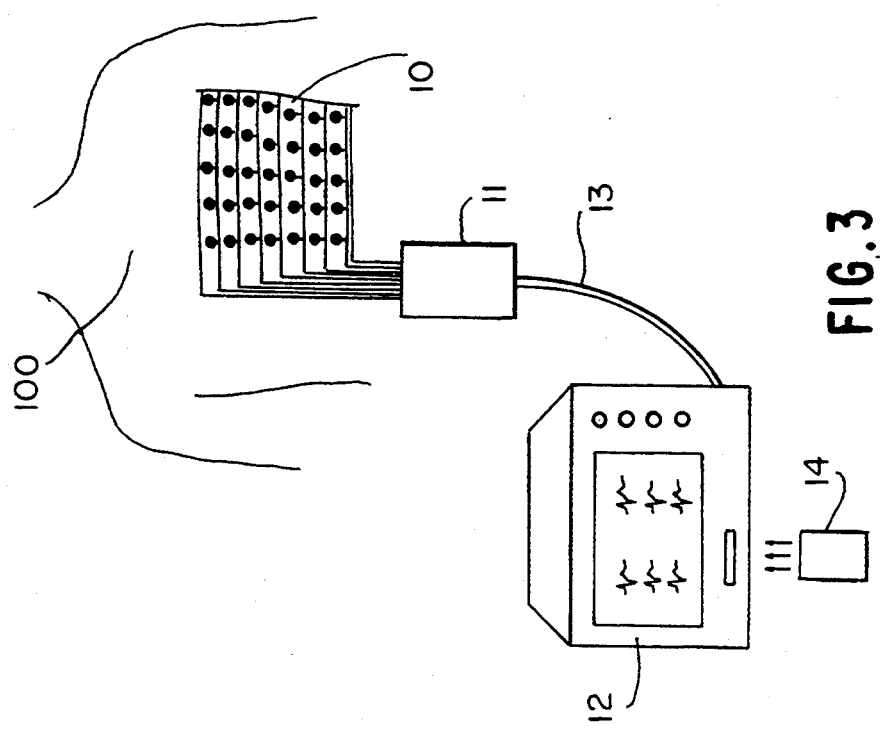
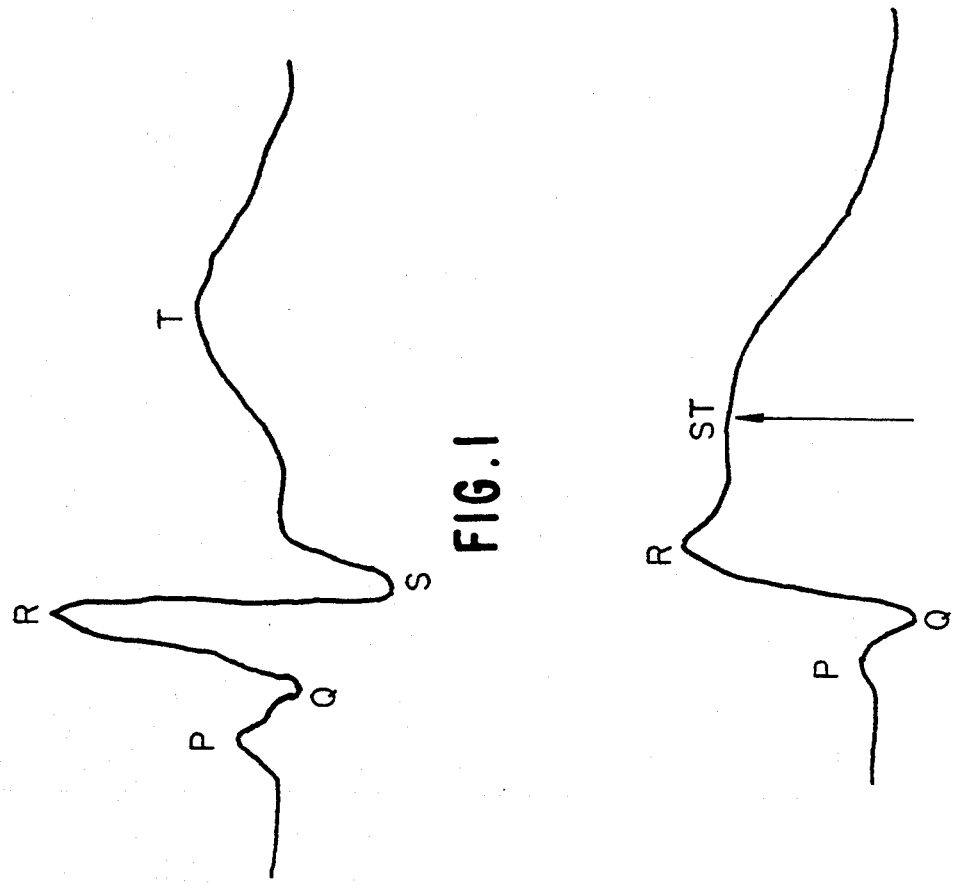

NON-INVASIVE MULTI-ELECTROCARDIOGRAPHIC APPARAATUS AND METHOD OF ASSESSING ACUTE ISCHAEMIC DAMAGE

BACKGROUND OF THE INVENTION

This invention relates to an apparatus and method for non-invasively detecting, digitally recording and processing cardiac generated electrical signals in the assessment of acute myocardial damage at the site of the victim's heart attack.

Electrical conduction in the human heart is initiated by a spontaneous electrical impulse at the sinoatrial node located at the top of the heart. This depolarising wave which spreads down the heart gives rise to heart muscle contraction and hence causes pumping of the blood. The ordered contraction of the heart muscle depends on an adequate supply of blood provided by the heart's own coronary arteries. Blockage "clot" of a coronary artery deprives a certain portion of cardiac muscle from receiving blood "ischaemia" and results in myocardial infarction. Myocardial ischaemia is a major cause of heart attacks and results in cardiac injury or even death to a high proportion of patients. Current medical intervention now provides "clot busting" thrombolytic drugs to remove the clot in the occluded coronary artery. These anti-clotting agents are given intraveneously on monitoring ischaemic damage. The potency or absorption rate of these drugs ensures rapid restoration of the ischaemic region by the reperfusion of blood. Since the majority of heart attacks occur outside hospital myocardial salvage will depend on the time taken to attend the patient and provide thrombolytic therapy.

A typical graph of cardiac generated potential of a normal heart beat is shown in FIG. 1, and consists of an isoelectric flat portion followed by a P wave, which is generated by the depolarisation of the atria, a QRS wave pattern, resulting from the depolarisation of the ventricles, and the T wave indicating repolarisation of the ventricles and termination of the heart beat. Initial ischaemic damage gives rise to the generation of "injury currents" through the chemical imbalance of these damaged muscle cells. This is reflected in the heart beat as elevation of the ST period as shown in FIG. 2 and the height provides an indication as to degree of damage. This electrical activity is at a maximum at the time of the heart attack and will change as infarction is caused or if thrombolytic therapy is provided.

Conventional electrocardiographs measure surface potentials from a limited number of locations i.e. a maximum of nine points. These twelve-lead electrocardiographic recorder/analyzers provide limited detection of ischaemic damage since they are primarily concerned with the interpretation of rhythm disorders. Heretofore it has only been considered necessary to monitor a small number of electrocardiograms in emergency situations in an attempt to detect myocardial ischaemia through some electrocardiograms showing sufficient elevated ST levels. This method, however, cannot detect all ischaemic regions throughout the heart and cannot provide assessment of the extent of the initial injury and therefore of subsequent recovery.

Clinical evaluations of myocardial infarction use blood enzyme tests and radio-isotope imaging which are invasive tests and cannot be used at the time of the attack and can only provide information hours after the event. They are, however, standardised clinical methods of reporting on myocardial infarction.

Body surface mapping systems are known. They are, however, concerned with providing detailed iso-potential contour plots and employ in the region of 200 leads. One known system, the Corazonix predictor BM-32 made by the Corazonix Corporation, of Oklahoma City, United States of America employs 32 leads. The system detects 32 electrocardiograms and, by extrapolation, and with further interpolation between these leads, provides a high definition of the geographical contour style mapping in the manner of a 192 lead system. This type of mapping system is then used in an attempt to differentiate normal patient distribution with suspected abnormal or infarct patients by using differencing maps. Articles by Robert L. Lux and others of the College of Medicine, University of Utah relate to the use of a large number of ECG leads. Their subsequent work shows that spatial redundancy may be achieved to reduce the 192 contour style lead system to 12 co-efficient waveforms. More recently the patent of Erwin R. John, 1990 (U.S. Pat. No. 4,974,598) employs multiple electrocardiogram statistical analysis in an attempt to provide a system or method for determining the presence of a wide range of heart disease conditions among a broader population. These current methods are concerned with the problems of contour style maps to identify abnormalities or sophisticated multiple statistical analysis in an attempt to identify a wide range of heart disorders. None of the known methods provides a technique in which the extent of the initial ischaemic injury, particularly within minutes of the commencement of a heart attack, can be determined.

SUMMARY OF THE INVENTION

It is an object of the present invention to provide a non-invasive apparatus and a method for rapidly determining the presence and extent of ischaemic injury at the onset of the symptoms, particularly when the use of thrombylitic therapy is being considered necessary.

The invention, therefore, provides an apparatus for the detection, recording and analysis of the electrical activity of a cardiac which apparatus comprises an array of a plurality of n number of electrodes, where n is an integer from 40–100, each of which is capable of detecting an electrical signal associated with the ST component of a heartbeat the array being connected to a microprocessor controlled interface which in turn is connected to a microprocessor controlled analyzer and display apparatus.

The invention also relates to a method of detecting, analysing and displaying electrical signals associated with the Q or ST or both waveforms of a heartbeat produced by an in vivo heart of an animal which comprises applying to the torso of the animal an array of a plurality of n number of electrodes where n is an integer from 40–100; amplifying the signal detected by each of the electrodes in an interface device; electronically grouping said signals into a plurality of groups of signals each group comprising from 2 to 20 electrode signals; digitising the amplified signals and feeding the digitised signals to a display, storage and processing (DSP) unit via a digital link connecting the unit with the interface; and displaying, storing and processing the digitised signals in the unit.

Preferably, the step of storing the digitised signals includes the step of recording the signals onto a memory card unique for that patient.

The apparatus and method according to the invention enables the objective measurement and computer analysis of Q or ST or both elevation maps and does not depend on the subjective interpretation of analog ECG waveforms or of topographic maps of body surface potentials or isopotential contours.

The medical problem is that heart attacks normally occur outside hospital and the victims have to be attended to by trained nurses and doctors. The present invention provides an apparatus and a method which is of practical diagnostic use in assessing ischaemic injury or infarct size, which is used at the location site of the cardiac victim and which presents information quickly so as not to impede emergency resuscitation.

Each of the electrodes of the array is juxtaposed in a different spatial location relative to the heart. Hence, each electrode detects a different potential pattern as generated from different sections of the heart which enables the presentation of the signal in such a manner as to enable the clinician to perceive a substantially three-dimensional picture of the condition of the heart, thereby enabling the clinician to assess the extent of the ischaemia. Successive heart beats are similarly monitored and, accordingly, the extent of ischaemic recovery can be continuously monitored with respect to a given time period. This time period may vary from a few minutes to a few hours or even days.

Essentially, therefore, the invention will enable the enhanced detection and size assessment of ischaemia as soon as possible after the attack. The provision of a plurality of electrodes at different points on the thoracic surface makes it is possible for a picture or map or fingerprint of the ischaemic area to be formed. Each electrode relates to electrical activity originating from different parts of the heart. The reconstructed body surface ST map can then be related to the depth and area size of the ischaemic region.

BRIEF DESCRIPTION OF THE DRAWINGS

The invention will be understood in greater detail from the following description of preferred embodiments thereof given by way of example only and with reference to the accompanying drawings in which:

FIG. 1 is a graphical representation of a single heartbeat of a typical normal heart;

FIG. 2 is a graphical representation of the Q and ST component of a single heartbeat of a heart immediately following the onset of a myocardial infarction or ischaemic heart disease;

FIG. 3 is a schematic view of the main components of a mapping device according to the invention;

DETAILED DESCRIPTION OF THE PREFERRED EMBODIMENT

Figure 4:
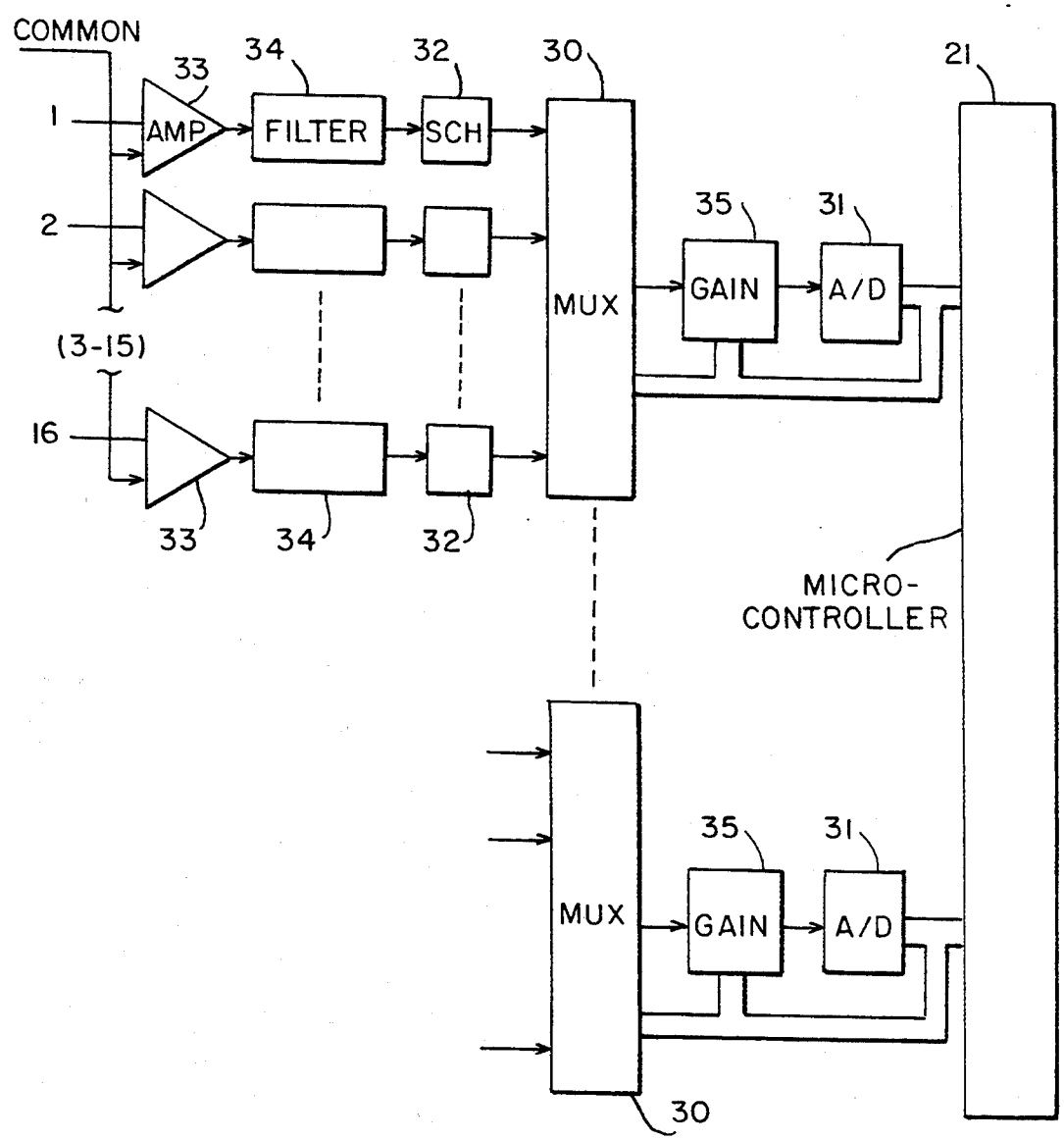
FIG. 4 is a schematic view of the amplification requirements of two of the signals of the mapping device according to the invention.

Referring now to the drawings, there is shown in FIG. 1 a graphical representation of a single heartbeat of a typical normal heart which has been described earlier in the Specification. FIG. 2 is a graphical representation of a single heartbeat of a heart immediately following the onset of a myocardial infarction or ischaemic heart disease which has been described earlier in the Specification.

The graphs shown in FIGS. 1 and 2 are derived from relatively low voltage electrical signals detected by electrodes located on the torso of a patient 100. It is the Q and/or the ST component of these signals which provide the data for enabling the present invention to detect the extent and severity of a myocardial infarction of ischaemic heart disease.

In the present invention, a removable two-dimensional array 10 of a plurality of electrodes is attached to the anterior surface of the torso of the patient 100. The number of electrodes in the array can vary from 40 to 100.

For a single heartbeat, each of the electrodes detects the electrical signal associated with, inter alia, the Q and/or the ST component of the heartbeat which signal has a strength in millivolts and requires high amplification (voltage ratio > 1000) before recordings can be obtained. A mapping unit 11 performs the front end amplification and analog to digital data conversion (FIG. 3). It will be appreciated that each electrode in the array 10, although detecting the same Q and/or the ST component of a single heartbeat, receives the signal with a different voltage having regard to their different spatial juxtapositions relative to each other and the heart.

The form of amplification employed is referred to as differential, since each electrode of the array 10 must be related to a common reference point known as the Wilson central terminal. This point is derived from the average of the sum of the limb lead points. The electronic amplifiers used are instrumentation differential amplifiers 33. These buffer the chest signals with ultra high input impedance (> 100M ohms) and high common mode rejection ratios (> 80 dB). The preamplified signals are then electrically filtered from 0.05 Hz–100 Hz in a filtering device 34 to further eliminate noise contamination such as DC polarisation and low/high frequency radiation and conduction. The total set of signals from the array 10 is divided into channels of 16 signals per channel (FIG. 4).

As FIG. 4 shows, the amplification on each signal is identical. Each signal is then frozen for a time period by a sample and hold device 32 so as to prevent signal phase distortion when these multiple signals are sequentially digitised. Each channel therefore contains 16 banks of amplification, filtering and sample/hold devices. A 16 to 1 analog signal multiplexer 30 is then used to sequentially switch through each of the 16 signals over the sample/hold period to enable a single channel digital conversion to be used. Prior to the digital conversion process a programmable gain circuit 35 is employed to allow a selection of common signal gain settings to be chosen by the operator in order to maximise overall signal strength. A microcontroller 21 controls the process of freezing the 16 analog signals and for this time period known as the sample/hold time the analog multiplexer is selected 16 times with each step sequentially switching through one of the 16 signals to the programmable gain circuit 35 and then into the analog digital converter 31. Therefore, the total number of signals captured is a multiple of the number of channels being used. Each channel and associated electronics may be accommodated onto a respective module all of which are then mounted in a compact unit which attaches directly to the array 10.

Although this embodiment shows 16 electrodes per channel, depending upon the total number of electrodes this will typically be from 2 to 20 electrode signals per channel.

The synchronised instantaneously sampled multiple data is then digitally transferred to the display, storage, and processing unit 12 via a direct digital link 13. The unit 12 contains a microcontroller board which polls each of the channels or modules to transfer sampled data onto a memory card 14 for total map recording. The unit 12 is also used for processing user input key operations and communicating to the display system the selected group of ECG strips. A display is necessary to serve as a means of interpreting the quality of the signals of each group of channels, for either gain selection or determining which electrodes may have poor skin contact. Once the patient hook-up is satisfactorily completed the recording method stores a pre-selected time frame (typically 5 seconds) of all the channels onto the memory card (typically 512 kbytes) for subsequent storage onto a permanent patient database in hospital.

Figure 5:
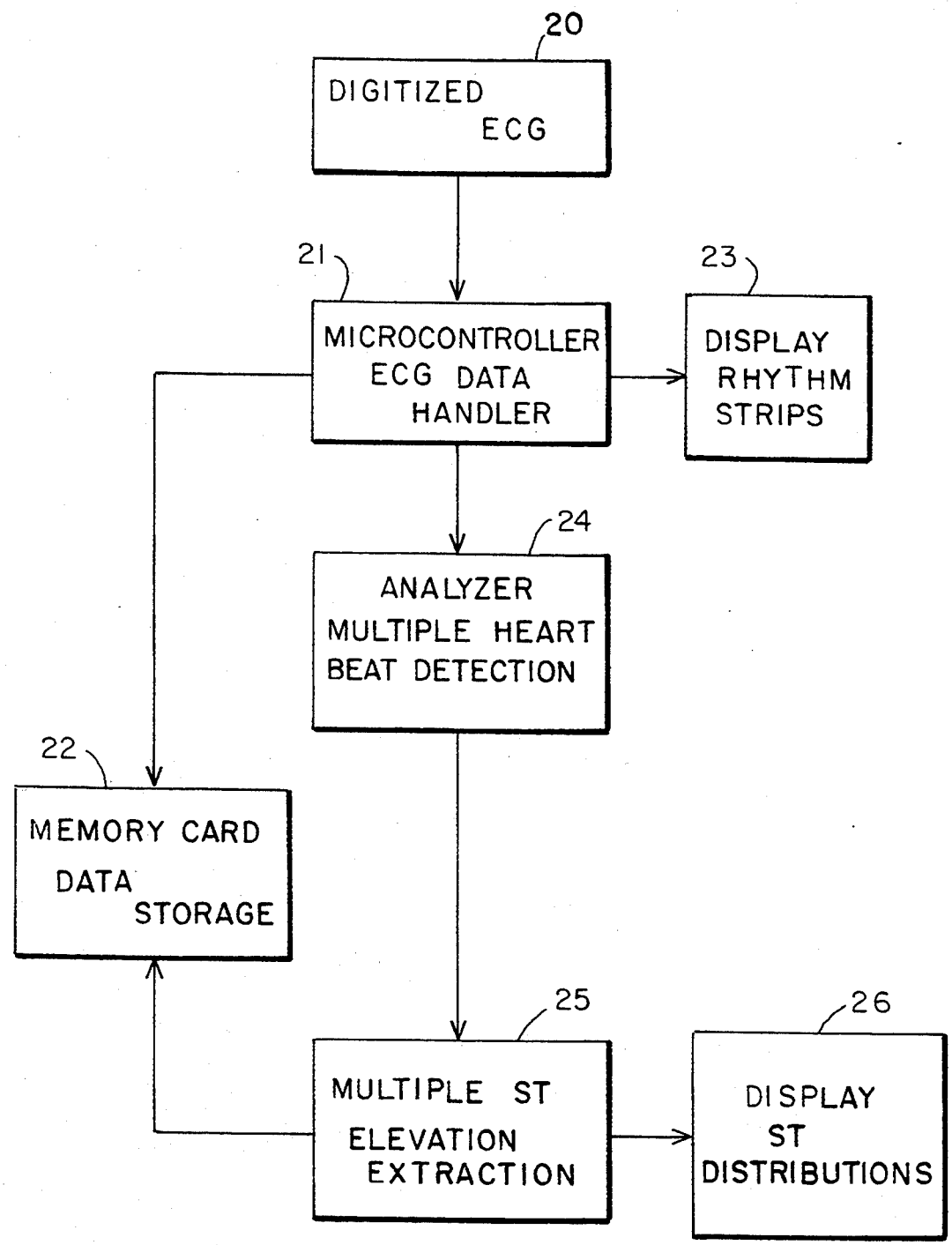
FIG. 5 is a block diagram of some of the components of the device according to the invention.
Figure 6:
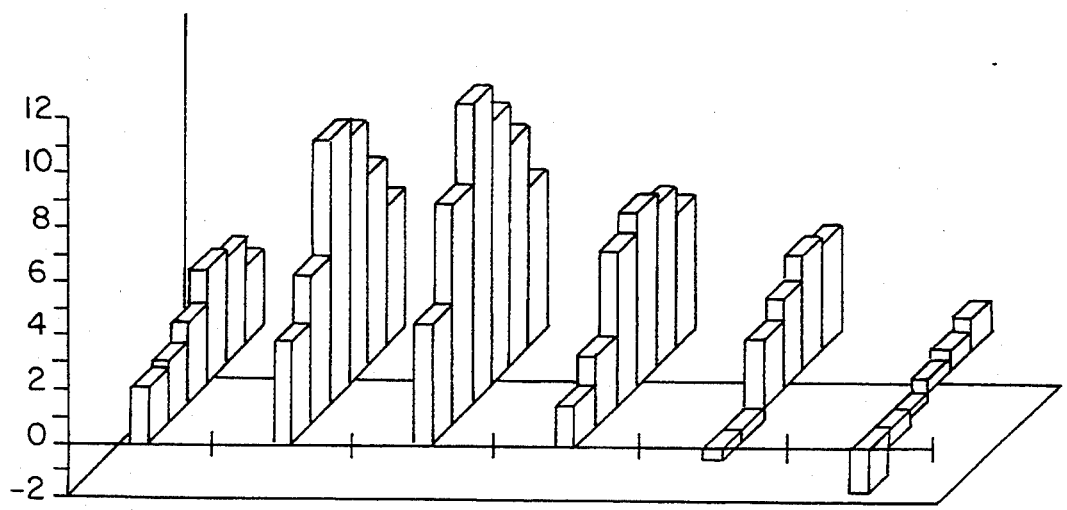
FIG. 6 is a representation of the ST component of a single heartbeat derived from signals received by a plurality of electrodes at the onset of an infarction.
Figure 7:
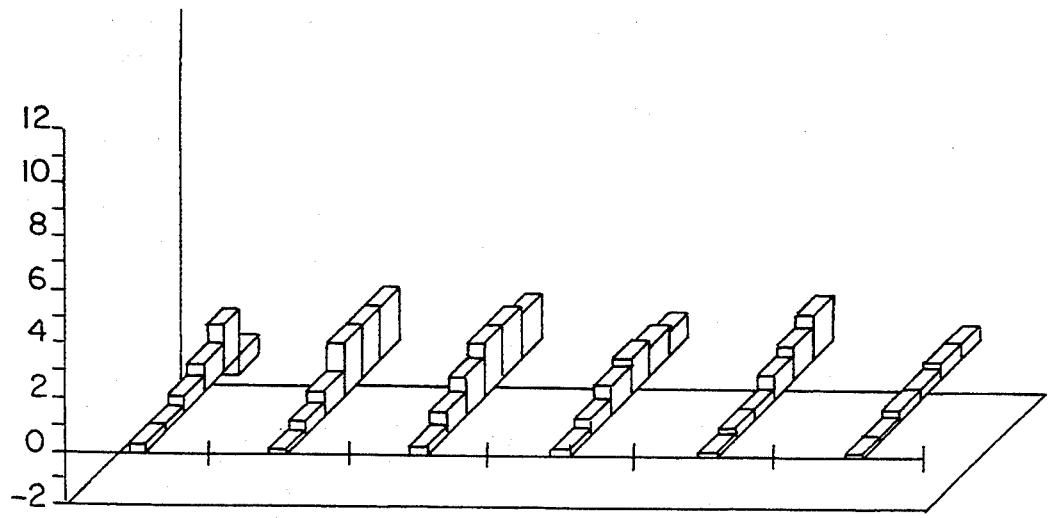
FIG. 7 is a representation similarly derived as in FIG. 6 but 90–120 minutes following onset of the infarction.

This analysis carried out by a further microprocessor computer section of the portable display unit 12 relates to the technique of graphically assessing ischaemic injury using data gathered and processed from the signals derived from the array 10. FIG. 5 shows the general digital ECG data flow and analysis. The microcontroller 21 receives the digitised data 20 and simultaneously transfers it to the memory card 22 and display module 23. The data is also simultaneously transferred to the microprocessor analyzer section 24 which performs automatic heartbeat detection, and the multiple ST elevation extracter 25 extracts the multiple ST elevations associated with each heartbeat. Each electrode provides an independent electrical picture of the heart when it is contracting as each one detects the summation of electrical changes in the heart from different angles or notional slices. Each picture or potential pattern will remain fairly constant from one heartbeat to the next in a normal contraction. Injury to the heart causes distortion or disturbance to this electrical activity and will result in changes in the potential pattern of those electrodes providing information on the injured area. The spread and depth of this damage causes more electrodes to change their potential pattern and the height of the ST component in each pattern. The multiple input signals are processed to extract the PQRST information. ST elevation (FIG. 2) is computed and selected as area under the ST segment or as a single or average value of at the ST segment taken at a fixed point into the ST segment relative to the S wave. Distribution information of the ST elevations is then displayed as a matrix of values or in a three dimensional bar/line or fishnet grid format. Calculating algorithms for calculating such formats are conventional as illustrated in the following publications: "Combined Manual For VidC & DigC" by Chirp Technical Services, pp.1—1 to 1-3; and Borland C++ Dos Reference, Version 4.0, p.54. This data is also stored on the memory card 22. This method of enabling the ischaemic injury to be assessed is shown in FIG. 6. The parameter known as ST level is an accepted measurement when detecting ischaemic injury in the standard twelve-lead system. Using the array 10 can now improve the accuracy of detecting ischaemic and infarct areas as well as of providing an estimate of the size of the damaged area. The method as presented here consists of producing a three dimensional profile of the ST levels processed from each electrode lead. Bar height or ST lead elevation refers to depth of damage as viewed from that specific electrode position. Therefore the overall damage can be quantified by the number of leads showing increased ST levels. This can be quickly reviewed by the doctor visually or as a statistical parameter. When ST maps are taken at different time periods and presented in this group format a better appreciation is given to the dramatic changes that take place when thrombolytic drugs are used to recover ischaemic injury. This recovery is reflected in the change or reduction of abnormal electrical activity, as can be seen in FIGS. 6 and 7. Therefore, this information which indicates the rate of resolution of the ST due to the absorption rate of the thrombolytic agent, can only be captured if the ECG's are recorded at the onset of the heart attack. Office or hospital based systems, therefore, cannot provide this information with respect to the initial picture of the injured area for patients incurring heart attacks outside hospital.

The multiple ECG maps are recorded as early as possible after the onset of symptoms of infarction. The electrode array 10 is attached to the anterior and part of the posterior surface of the thoracic torso. The simplified array 10 can make it possible to quickly apply and record from these multiple electrode sites on the chest wall. Should ventricular fibrillation develop rapid removal of the electrode array 10 is possible. During the initial period of acute myocardial infarction the only immediate changes are contained in the ST segment of the ECG. At this time equipotential maps are of little use because the ischaemic area has not yet developed. The ST maps produced from this portable system allow immediate patient management of the acute myocardial infarction and with the intervention of thrombolytic drugs will optimise the patient treatment. The ST map will normally change as the ischaemic damage develops and unless used at the site of the attack this data will be lost.

The present invention provides a system and a method that allows immediate recording and processing of the electrical activity at the site of the heart attack. The portable processing of these multiple electrograms and in particular ST maps will increase the sensitivity of ischaemic damage, thereby improving the need for thrombolytic therapy and also providing a method of qualifying these drugs.

The present invention also provides a method of allowing ST map monitoring during transport of the patient.

The present invention also provides a form of presentation of 3-dimensional Q or ST or both maps for clinical evaluation.

The invention is not limited by or to the specific embodiments described which can undergo considerable variation without departing from the scope of the invention.

We claim:

1. An apparatus for the detection and display of the electrical activity of an animal heart, said apparatus comprising: a 2-dimensional array of a number n of electrodes, where n is an integer from 40 to 100, for individually detecting an electrical signal associated with the ST component of a heartbeat, interface means for converting an output signal of each electrode to digital form, and display means responsive to the digital signals to provide a 3-dimensional graphical display of the ST component levels detected by the electrodes as a measure of cardiac condition.

2. An apparatus as claimed in claim 1, wherein the interface means includes a respective amplifying and sample/hold means for each electrical signal, a plurality of multiplexers less than the number of electrodes, each multiiplexer having a plurality of inputs respectively connected to the outputs of a plurality of sample/hold means, and an analog to digital converter connected to the output of each multiplexer.

3. An apparatus as claimed in claim 2, wherein each multiplexer has from 2 to 20 inputs.

4. An apparatus as claimed in claim 1, wherein the detection and display apparatus includes means for recording the digital signals onto a memory card.

5. A method for the detection and display of the electrical activity of an animal heart, comprising the steps of: applying to the torso of the animal a 2-dimensional array of a number n of electrodes, where n is an integer from 40 to 100, detecting with each electrode an electrical signal associated with the ST component of a heartbeat, converting an analog output signal from each electrode to digital form, and producing from the digital signals a 3-dimensional graphical display of the ST component levels detected by the electrodes.

* * * * *